United States Patent
Ramos et al.

(10) Patent No.: US 11,922,824 B2
(45) Date of Patent: Mar. 5, 2024

(54) INDIVIDUALIZED MEDIA PLAYBACK PACING TO IMPROVE THE LISTENER'S DESIRED OUTCOMES

(71) Applicant: INTERNATIONAL BUSINESS MACHINES CORPORATION, Armonk, NY (US)

(72) Inventors: Igor S. Ramos, Round Rock, TX (US); Angelo Danducci, II, Austin, TX (US); Kimberly J. Taft, Austin, TX (US); Devon E. Mensching, Austin, TX (US)

(73) Assignee: International Business Machines Corporation, Armonk, NY (US)

( * ) Notice: Subject to any disclaimer, the term of this patent is extended or adjusted under 35 U.S.C. 154(b) by 35 days.

(21) Appl. No.: 17/656,004

(22) Filed: Mar. 23, 2022

(65) Prior Publication Data
US 2023/0326358 A1    Oct. 12, 2023

(51) Int. Cl.
| | | |
|---|---|---|
| *G09B 5/04* | (2006.01) | |
| *A61B 5/16* | (2006.01) | |
| *G06F 3/16* | (2006.01) | |
| *G10L 15/18* | (2013.01) | |
| *G09B 21/00* | (2006.01) | |

(52) U.S. Cl.
CPC ............... *G09B 5/04* (2013.01); *A61B 5/165* (2013.01); *G06F 3/165* (2013.01); *G10L 15/1815* (2013.01); *A61B 2503/12* (2013.01); *G09B 21/006* (2013.01)

(58) Field of Classification Search
CPC ........... G09B 5/04; A61B 5/165; G06F 3/165; G10L 15/1815
See application file for complete search history.

(56) References Cited

U.S. PATENT DOCUMENTS

| | | |
|---|---|---|
| 6,374,225 B1 | 4/2002 | Hejna, Jr. |
| 6,490,553 B2 | 12/2002 | Van Thong |
| 8,332,212 B2 | 12/2012 | Wittenstein |
| 8,849,948 B2 | 9/2014 | Gilson |
| 9,741,392 B2 | 8/2017 | Ngiam |
| 9,916,127 B1 | 3/2018 | Abou Mahmoud |
| 10,158,825 B2 | 12/2018 | Abou Mahmoud |
| 10,250,925 B2 | 4/2019 | Agrawal |
| 10,863,216 B2 | 12/2020 | Chi |

(Continued)

OTHER PUBLICATIONS

Bailenson, "Detection of Comprehension & Emotion from Real-time Video Capture of Facial Expressions," mediaX at Stanford University [online], [accessed on Jan. 31, 2022], 4 pages, Retrieved from the Internet: <URL: https://mediax.stanford.edu/research-projects/hmi-bailenson/>.

(Continued)

*Primary Examiner* — Kesha Frisby
(74) *Attorney, Agent, or Firm* — Robert D. Bean

(57) ABSTRACT

According to one embodiment, a method, computer system, and computer program product for personalizing playback of an audio stream is provided. The present invention may include sectioning the audio stream into one or more content blocks and one or more filler blocks; determining one or more topics associated with the one or more filler blocks; determining a level of complexity associated with the one or more filler blocks; determining a listener's level of interest in and level of comprehension of the one or more topics; based on the level of complexity, the level of interest, and level of comprehension corresponding to the one or more topics, assigning a playback speed to the one or more content blocks associated with the one or more topics; and modifying the one or more content blocks to play at the assigned playback speed.

20 Claims, 7 Drawing Sheets

(56) References Cited

U.S. PATENT DOCUMENTS

2006/0036783 A1    2/2006   Aarts
2006/0084047 A1    4/2006   Chiu
2007/0250311 A1   10/2007   Shires
2009/0319265 A1   12/2009   Wittenstein
2017/0322766 A1   11/2017   Thörn

OTHER PUBLICATIONS

Bailenson, et al., "Real-time classification of evoked emotions using facial feature tracking and physiological responses," International Journal of Human-Computer Studies, May 2008, pp. 303-317, vol. 66, Issue 5, doi:10.1016/j.ijhcs.2007.10.011, Retrieved from the Internet: <URL: https://www.sciencedirect.com/science/article/abs/pii/S1071581907001462>.

IBM, "Watson Natural Language Understanding," IBM.com [online], [accessed on Jan. 31, 2022], 7 pages, Retrieved from the Internet: <URL: https://www.ibm.com/cloud/watson-natural-language-understanding>.

Mell, et al., "The NIST Definition of Cloud Computing", National Institute of Standards and Technology, Special Publication 800-145, Sep. 2011, 7 pages.

Van Den Rul, "[NLP] Basics: Measuring the Linguistic Complexity of Text", Towards Data Science [online], Nov. 9, 2019 [accessed on Jan. 31, 2022], 10 pages, Retrieved from the Internet: <URL: https://towardsdatascience.com/linguistic-complexity-measures-for-text-nlp-e4bf664bd660>.

Wikipedia, "Competency-based learning", Wikipedia, the free encyclopedia, [accessed on Jan. 31, 2022], 3 Pages, Retrieved from the Internet: <URL: https://en.wikipedia.org/wiki/Competency-based_learning>.

INDIVIDUALIZED MEDIA PLAYBACK PACING TO IMPROVE THE LISTENER'S DESIRED OUTCOMES

BACKGROUND

The present invention relates, generally, to the field of computing, and more particularly to educational technology.

Educational technology is the combined use of computer hardware, software, and educational theory and practice to facilitate learning, and is concerned with improving learning outcomes through the development and application of new technologies combined with educational theories and methods. One major tool of educational technology since the popular advent of radio and later, home computers and cell phones, is audible media. Audible media such as podcasts, videos, and audio learning materials are more prevalent today than ever before as the result of the rise of remote schooling and working from home and are being used by many as a way to supplement learning. However, audible media still faces challenges in realizing its full educational potential, and the field of educational technology can stand to benefit from developing technologies in improving the listening comprehension of audible media consumers.

SUMMARY

According to one embodiment, a method, computer system, and computer program product for personalizing playback of an audio stream is provided. The present invention may include sectioning the audio stream into one or more content blocks and one or more filler blocks; determining one or more topics associated with the one or more filler blocks; determining a level of complexity associated with the one or more filler blocks; determining a listener's level of interest in and level of comprehension of the one or more topics; based on the level of complexity, the level of interest, and level of comprehension corresponding to the one or more topics, assigning a playback speed to the one or more content blocks associated with the one or more topics; and modifying the one or more content blocks to play at the assigned playback speed.

BRIEF DESCRIPTION OF THE SEVERAL VIEWS OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. In the drawings.

DETAILED DESCRIPTION

Figure 1:
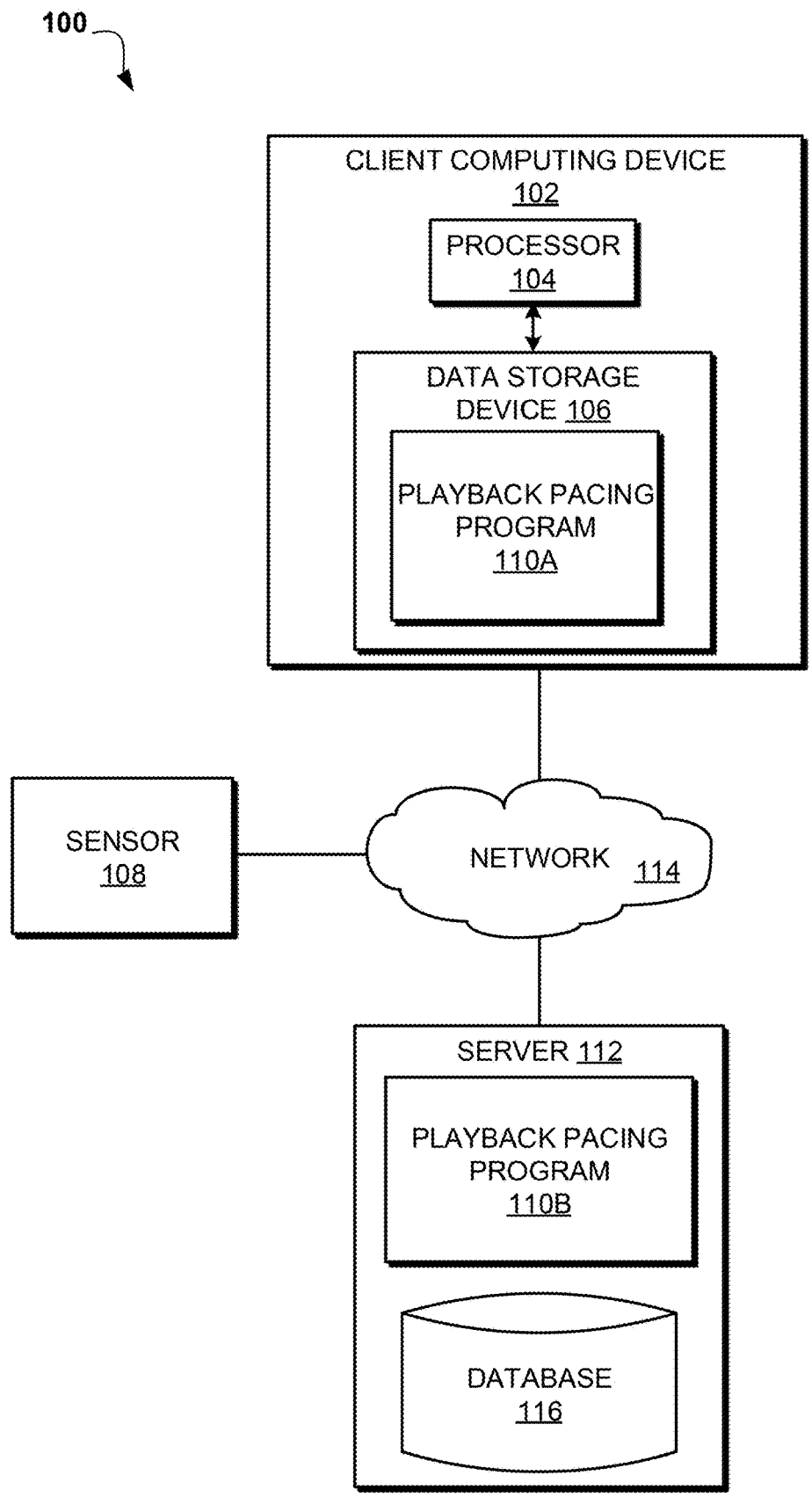
FIG. 1 illustrates an exemplary networked computer environment according to at least one embodiment.

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. In the description, details of well-known features and techniques may be omitted to avoid unnecessarily obscuring the presented embodiments.

As previously described, educational technology is the combined use of computer hardware, software, and educational theory and practice to facilitate learning, and is concerned with improving learning outcomes through the development and application of new technologies combined with educational theories and methods. One major tool of educational technology since the popular advent of radio and later, home computers and cell phones, is audible media. Audible media such as podcasts, videos, and audio learning materials are more prevalent today than ever before as the result of the rise of remote schooling and working from home and are being used by many as a way to supplement learning. However, quality and cadence of audible media varies greatly between and even within these mediums. It is commonly accepted that the best rate of speech to promote listening comprehension is between 140-160 words per minute. However, this is not universally true, and may change based on the listener's prior knowledge of the subject discussed, as well as the complexity of the subject matter. Additionally, listeners have a limited time to dedicate to learning and often lose interest if the content is not relevant to their interests or learning goals. While many media players offer listeners the ability to perform a flat rate change to an existing audio stream, for example by changing the speech playback or skipping ahead manually, this method suffers from several drawbacks; first of all, it requires that the listener manually engage with the audible media player to make changes. Furthermore, the audible media players often offer an oversimplified interface, with limited selection and granularity in playback speeds (0.5× speed, 1.5× speed, 2× speed), and may not offer the right speed for a given listener. Furthermore, a listener may not even know what speed best facilitates their own listening comprehension, and as the topic changes and the speed best suited for a listener's listening comprehension changes in response, the listener may not adjust the speed in response to the topic changes, potentially degrading comprehension. Additionally, visually impaired persons may not be able or as able to manually change the playback speed. As such, it may be advantageous to, among other things, implement a system that creates a personalized media playback pacing for each topic in a given audible media stream based on the complexity and context of the topic and associated content block, listener preferences at time of media consumption, listener learning goals and interests, listener familiarity with the subject matter, and historical crowdsourced data, and automatically applying the personalized media playback pacing on a per-topic basis.

Embodiments of the present invention relate to the field of computing, and more particularly to educational technology.

The following described exemplary embodiments provide a system, method, and program product to, among other things, create a personalized media playback pacing based on the media content and listener data at the time of media consumption. Therefore, the present embodiment has the capacity to improve the technical field of educational technology by utilizing natural language processing techniques to modify digital audible media files in a way that is tailored to individual listeners on a per-topic basis and improves the listening comprehension of the listener with respect to the audible media, thereby improving the learning potential of the audible media and improving learning outcomes for listeners of the audible media. The present embodiment addresses at least the technical problem of visually-impaired listeners being unable to engage with graphical speed control elements of audible media players, and the technical problem of current audible media players failing to offer playback speed and cadence settings that are best suited to a given listener.

According to one embodiment, the invention is a system that analyzes an audio stream, sections the audio stream into content blocks and filler blocks, determines the subject matter and complexity of the content blocks, determines a level of interest and a level of comprehension of the subject matter topics for a listener, and assigns an audio speed to the content blocks.

In some embodiments of the invention, the audio stream, or audible media, may be any digital file comprising an audio component which in turn comprises recorded human speech. In some embodiments of the invention, the audio stream may refer to a digital file that is in the process of being delivered piecemeal in the form of data packets through a network connection, which may be occurring in real time or near-real-time as the audio stream is being created, for instance as human speech is being recorded. The audio stream may be defined as belonging to a particular format of audio stream based on how the speech in the audio stream is organized. Examples of formats may include podcasts, lectures, radio shows, instructional videos, et cetera. The audio stream may be part of a series, where a series may comprise a plurality of audio streams related through common speakers, common names, common topics, et cetera. The audio stream may comprise content blocks and filler blocks.

In some embodiments of the invention, filler blocks may be speech or music/sounds that do not serve a substantive learning or entertainment purpose. In other words, filler blocks might be any component of the audible media which is not associated with a topic. General examples of filler blocks may include advertisements, instrumental music, introductory or transitional segments, outros, credits, sound effects, intermissions, et cetera. In some embodiments of the invention, filler blocks may further comprise core talking points.

In some embodiments of the invention, content blocks may be substantive sections of the audible media that pertain to a single topic, and which a listener may benefit from improving comprehension of. Examples of content blocks may include a lecture about a historical event in a history class, a discussion of a particular current event in a podcast, a lecture about the rise of green energy, et cetera. In some embodiments of the invention, for example where audible media comprises a large number of topics, the content block may comprise a number of subtopics, which are topics that can be unified within a single broader topic; for example, in a podcast where the show is about the evolution of printing technology, and during which the hosts discuss the state of printing technology three different eras, 1400 s, 1800 s, and modern, the topic may be the evolution of printing technology, and the 1400 s, 1800 s, and modern eras may comprise individual subtopics. In some embodiments of the invention, the system may consider the entire discussion on the topic of the evolution of printing technology to be a content block; in some embodiments of the invention, the system may consider the three subtopics to correspond to individual content blocks.

In some embodiments of the invention, the system may analyze the audio stream by using natural language processing techniques to identify and extract natural language and transcribe the natural language into a text format for further analysis and annotation. Analyzing the audio stream may include speech segmentation to split the speech into words, part of speech tagging to identify the part of speech of each word, syntactic analysis to identify, among other things, sentence breaks and punctuation marks, et cetera.

In some embodiments of the invention, the system may section the audio stream into content blocks and filler blocks. The system may analyze the text comprising the transcript of the audio stream to determine what portions of the text comprise content blocks and what portions of the text comprise filler blocks and add annotations to the transcript delineating the sections. The system may detect and tag filler content using supervised learning techniques against known recurring filler content such as musical segues, introduction material such as phrases including "subscribe to my channel" or "hi welcome to the show," advertising phrases such as "this show brought to you by . . . " or "and now a word from our sponsor," et cetera. In some embodiments of the invention, the system may tag any speech that is not considered filler blocks as content blocks; in some embodiments of the invention, the system utilizes supervised learning techniques against known recurring characteristics of content blocks, such as phrases including "what we're seeing here is" or "what you have to understand is."

In some embodiments of the invention, the system may analyze the prosody of the natural language in the audio stream instead of or in addition to the text transcript, and identify filler blocks and content blocks, and/or the transition between segments, by using supervised learning techniques against known recurring prosodic elements associated with filler blocks or content blocks, in some embodiments associated with specific speakers and/or series of audio streams. For example, a rising intonation pattern may indicate the beginning of a segment, circumflex intonations may mark the substance of the segment, and a downward inflection pattern may indicate the end of a segment. Particular speakers in a media stream may utilize a particular cadence and rhythm when performing advertisements, and some may utilize a particular cadence and rhythm when discussing topics.

In some embodiments of the invention, the system may utilize a template in sectioning the audio stream. The template may be associated with a particular format and/or series of audio stream and may comprise a list of general sections of the audio stream that all or many audio streams of the same format or series associated with the template follow. An exemplary template for a podcast is depicted below:

PODCAST SCRIPT (TEMPLATE)

1. Opening: A quick musical jingle.
2. Introduction: A monologue style introduction introducing your hosts and what you will talk about on your show.
3. Segue: Could be music or a sound effect.
4. Topic 1: Talk for about 3 minutes.

5. Vocal segue: "We are going to move on and talk about . . . "
6. Topic 2: Talk for about 3 minutes.
7. Sponsored message or podcast advertisement.
8. Musical segue
9. Topic 3: Talk for about 3 minutes.
10. Closing remarks: Thank the audience, guests, introduce what will be on the next show.
11. Closing musical jingle.

The system may section the audio stream according to the template, using the pre-provided sections as a guide to dividing the natural language into sections, and identifying which of the pre-provided sections comprise filler blocks and which comprise content blocks. In some embodiments of the invention, the template may have the sections pre-labeled as comprising filler blocks or content blocks.

In some embodiments of the invention, the system may determine the subject matter of the content blocks by analyzing the discourse semantics of the audio stream to perform topic segmentation and recognition. Topic segmentation and recognition may be achieved using any number of methods, including, for example, Hidden Markov Models, lexical chains, passage similarity using word co-occurrence, clustering, topic modeling, et cetera. In some embodiments of the invention, the system may initially section the audio stream into filler blocks and non-filler blocks and use topic segmentation and recognition to identify the topics of the non-filler blocks and accordingly divide the non-filler blocks into content blocks based on the topics. The system may annotate the transcript and/or the audio stream to record each topic and the content block with which the topic is associated.

In some embodiments of the invention, the system may determine the complexity of the content blocks. The system may measure the linguistic complexity of the content blocks as a function of lexical readability and/or lexical richness. Lexical readability may be a metric of complexity based on how hard a text is to read, and may be, for example, a function of the average sentence length and average word syllables of the content block. Lexical richness may be a metric of complexity based on the variety of unique words, and may be, for example, a function of the total number of unique words in the content block or the number of words that only occur once divided by the total number of words. In some embodiments of the invention, the system may determine the complexity of the content blocks based on the topic; for example, general and/or simple topics, such as "pop culture news" or "cute animal reactions," may require very little background knowledge, familiarity, or concentration to digest. On the other hand, more specific and detailed topics, such as "discussion of three-photon interference" or "effects of Alice on patent examination 2013-present" may require specialized knowledge in or familiarity with dense technical fields, and/or may require above-average concentration to comprehend. Based on the complexity analysis, the system may assign a complexity score to each of the content blocks.

In some embodiments of the invention, the system may determine a level of interest of the listener with respect to the topics. The level of interest may be based on any number of combination of indications of interest entered by the listener, listening history associated with the listener, personal interests of the listener, and learning goals entered by the listener. The indication of interest entered by the listener may be an explicit indication of topics and/or formats and/or series of audio streams that the listener is interested in listening to, entered into the system for example in response to a prompt or survey. The historical data may include audio streams that the listener has listened to in the past. The personal interests of the listener may be topics that the listener may be interested in listening to audio streams about, extrapolated for example based on a similarity to the listener's expressed interests, listening history, et cetera. The learning goals may be topics which the listener has expressed a desire to learn more about or to acquire a deep understanding of, for example in response to a prompt sent by the system; while a listener may be interested in some topics, the listener may desire a deeper understanding of topics that the listener is not necessarily interested in, for example tax preparation or business operations, and which therefore may not be necessarily reflected in the listener's personal preferences. In some embodiments of the invention, the learning goals may further comprise an amount of total time the listener has available to listen to the audio stream, and/or an amount of time the listener wants to spend on certain topics. In some embodiments of the invention, the learning goals may comprise a preferred level of comprehension, which represents the level of comprehension that the listener wants to achieve for a given topic. For example, whether the listener just wants an overview of a topic or whether the listener wants to comprehend the topic on a deeper level. The system may, for any given topic, generate an interest score associated with the listener based on the determined level of interest.

In some embodiments of the invention, the system may determine a level of comprehension of the listener with respect to the topics. The level of comprehension may be based on, for example, the listener's self-assessment, listening history of the listener, and learning assessments such as competency-based learning. The listener may be prompted to assess their own comprehension of a given topic. The system may also infer level of comprehension from the listening history of the listener; if the listener has listened to many content blocks in the past that were on topics similar to the topics in the current audio stream, the system may infer that the listener has a high level of comprehension for the topic. The level of comprehension may be based on how quickly the listener picked up concepts or new topics in the past. In some embodiments of the invention, for example where the listener's comprehension of the topic was inferred from sentiment which was in turn inferred from sensor data from biometric sensors while listening to the audio stream, the level of comprehension may be based on past comprehension assessments of similar topics. The system may assign a comprehension score to a given topic based on the level of comprehension associated with the listener.

In some embodiments of the invention, the system may assign a playback speed, or playback pacing, to the content blocks of the audio stream. For content blocks associated with dense topics, or topics where the complexity score associated with the content block exceeds an upper complexity threshold, the system may normalize the assigned playback speed of the content block to a lower default speed value, which may be, for example, 140 words per minute. For content blocks associated with topics that are easy to comprehend, or topics where the complexity score of the content block falls below a lower complexity threshold, the system may normalize the assigned playback speed of the content block to an upper default speed value, for example 160 words per minute. The system may then adjust the assigned playback speed of these starting speed values upwards or downwards based on the comprehension score and interest score associated with the listener, and the complexity score associated with the content block. For example, as the complexity score associated with the content block falls, the comprehension scores and/or interest scores associated with the listener rise, the higher the playback speed that the system assigns to the content block. This reflects the fact that the less complex a content block is, the better equipped a listener is to comprehend the content block, and/or the more interested a listener is in the content block, the easier the content block will be to comprehend for the listener, the higher playback speeds at which the system may play the content block without negatively affecting the listener's comprehension of the subject matter of the content block, and the faster and more efficient the listener may be in absorbing the subject matter of the content block. Conversely, as the complexity score associated with the content block rises, the comprehension scores and/or interest scores associated with the listener fall, the lower the playback speed that the system assigns to the content block. This reflects the fact that the more complex a content block is, the less equipped a listener is to comprehend the content block, and the less interested a listener is in the content block, the lower the playback speeds a listener requires to fully absorb the contents of the content block, and the lower the playback speeds at which the system must accordingly play the content block in order to best facilitate comprehension of the content block. For example, sports news highlights are simple and easy to comprehend and can be listened to at high speeds, while physics lectures are dense and difficult to comprehend and must be listened to at a lower speed. Once the system has applied the effects of the complexity, comprehension, and interest scores to the default speed values, the system may assign the playback speed to the content block.

In some embodiments of the invention, for example where the learning goals comprise an amount of total time the listener has available to listen to the audio stream, and/or an amount of time the listener wants to spend on certain prioritized topics, the system may further adjust the playback speed of the content blocks to conform to the listener's learning goals, for example by increasing the playback speed of content blocks associated with topics the listener has not prioritized to allow the listener to spend the desired amount of time on the content blocks associated with prioritized topics, and/or to allow playback of the content blocks associated with prioritized topics to proceed at speeds low enough to allow full listener comprehension. In some embodiments, for example where the learning goals comprise a preferred level of comprehension that a listener wants to achieve for a given topic, the system may adjust the playback speed to facilitate achieving the preferred level of comprehension. For example, the system may decrease playback speed for content blocks associated with topics regarding which the listener would prefer to achieve full comprehension, and/or may increase playback speed for content blocks associated with topics regarding which the listener only desires an overview.

In some embodiments of the invention, the system may apply the assigned playback speed to the content block by ingesting the audio stream and depending on the native playback speed of the content block relative to the assigned playback speed, speed up or slow down playback of the audio stream, for example by synthesizing speech based on the transcript at the desired playback speed.

In some embodiments of the invention, the system may additionally or alternatively modify the audio stream by partially or entirely removing filler blocks, and/or by partially or entirely removing content blocks, for example removing those content blocks pertaining to topics for which the listener's interest score and/or comprehension score falls below a minimum threshold or removing sections of the content block that are not related to a prioritized topic. For instance, the system may operate according to the following example: John is about to watch an audio stream comprising a lecture in security that is an hour long at its native playback speed. The system identifies ten topics comprising the audio stream and determines that John has a weak understanding of five of those topics. Based on John's stated available listening time of fifteen minutes, and his previously stated interest in mutual transport layer security (mTLS), the system tailors the one-hour lecture to be delivered in fifteen minutes, by removing filler blocks and content blocks/content block sections that are neither associated with mTLS nor constitute enabling background for that topic.

In some embodiments of the invention, the system may, based on real-time biometric information of the listener, dynamically modify the audio speed of the content blocks during playback of the audio stream to the listener. The system may, using sensors such as cameras or EEG machines, and subject to listener's approval, collect real-time biometric data to determine a listener's level of comprehension based on a detected sentiment of the listener in real time as the listener is listening to the audio stream. The listener's sentiment may include confusion or frustration, which may be, for example, inferred from sensor data indicating dilated pupils, an elevated heart rate, furrowing of the brow, frowning, exasperated noises, et cetera. The listener's sentiment may further include boredom, which may, for example, be inferred from sensor data indicating above-average eye movement, yawning, fidgeting, sighing, et cetera. The system may perform remedial actions based on detecting certain sentiments of the listener. For example, if the system determines, based on the sensor data, that the listener is expressing confusion or frustration, the system may decrease the playback speed of the current content block or repeat all or part of the current content block to allow the listener more time to process the content block, improving comprehension and reducing frustration. If the system determines based on the sensor data that the listener is expressing distraction or boredom, the system may increase playback speed of the current content block to increase the listener's stimulation and increase interest or may skip the current content block and/or move to a content block associated with a topic that has a higher interest score. In some embodiments of the invention, the system may adjust the complexity scores, interest scores, and/or comprehension scores of a listener with respect to the topic of the currently consumed content block. In some embodiments of the invention, the system may perform remedial actions based on both detecting sentiments of the listener and determining that the listener indicated, for example through learning goals, a desire to fully or significantly comprehend the topic of the current content block.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The following described exemplary embodiments provide a system, method, and program product to create a personalized media playback pacing based on the media content and listener data at the time of media consumption.

Referring to FIG. 1, an exemplary networked computer environment 100 is depicted, according to at least one embodiment. The networked computer environment 100 may include client computing device 102 and a server 112 interconnected via a communication network 114. According to at least one implementation, the networked computer environment 100 may include a plurality of client computing devices 102, sensors 108, and servers 112, of which only one of each is shown for illustrative brevity.

The communication network 114 may include various types of communication networks, such as a wide area network (WAN), local area network (LAN), a telecommunication network, a wireless network, a public switched network and/or a satellite network. The communication network 114 may include connections, such as wire, wireless communication links, or fiber optic cables. It may be appreciated that FIG. 1 provides only an illustration of one implementation and does not imply any limitations with regard to the environments in which different embodiments may be implemented. Many modifications to the depicted environments may be made based on design and implementation requirements.

Client computing device 102 may include a processor 104 and a data storage device 106 that is enabled to host and run a playback pacing program 110A and communicate with the server 112 via the communication network 114, in accordance with one embodiment of the invention. Client computing device 102 may be, for example, a mobile device, a telephone, a personal digital assistant, a netbook, a laptop computer, a tablet computer, a desktop computer, or any type of computing device capable of running a program and accessing a network. As will be discussed with reference to FIG. 5, the client computing device 102 may include internal components 502a and external components 504a, respectively.

The server computer 112 may be a laptop computer, netbook computer, personal computer (PC), a desktop computer, or any programmable electronic device or any network of programmable electronic devices capable of hosting and running a playback pacing program 110B and a database 116 and communicating with the client computing device 102 via the communication network 114, in accordance with embodiments of the invention. As will be discussed with reference to FIG. 5, the server computer 112 may include internal components 502b and external components 504b, respectively. The server 112 may also operate in a cloud computing service model, such as Software as a Service (SaaS), Platform as a Service (PaaS), or Infrastructure as a Service (IaaS). The server 112 may also be located in a cloud computing deployment model, such as a private cloud, community cloud, public cloud, or hybrid cloud.

Sensor 108 may be any sensor capable of capturing real-time sentiment metrics, including visual and infrared cameras, electroencephalography (EEG) sensors, microphones, accelerometers, motion detectors, vitality trackers, et cetera. Sensor 118 may also be enabled to communicate with network 114 or may be integrated into or otherwise in communication with client computing device 102 or server 112.

According to the present embodiment, the playback pacing program 110A, 110B may be a program capable of create a personalized media playback pacing based on the media content and listener data at the time of media consumption. The playback pacing program 110A, 110B may be located on client computing device 102 or server 112 or on any other device located within network 114. Furthermore, playback pacing program 110A, 110B may be distributed in its operation over multiple devices, such as client computing device 102 and server 112. The playback pacing method is explained in further detail below with respect to FIG. 2.

Figure 2:
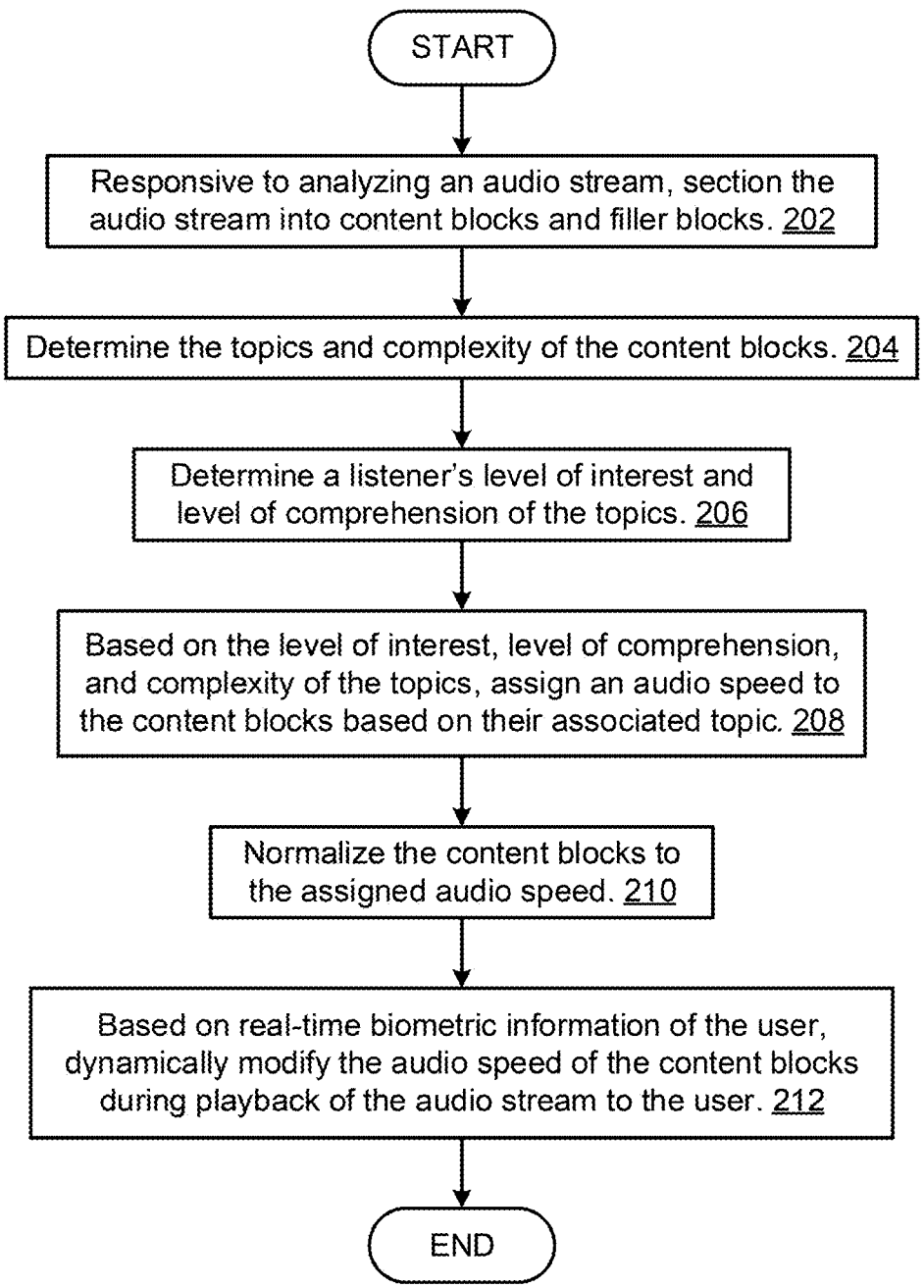
FIG. 2 is an operational flowchart illustrating a playback pacing process according to at least one embodiment.

Referring now to FIG. 2, an operational flowchart illustrating a playback pacing process 200 is depicted according to at least one embodiment. At 202, the playback pacing program 110A, 110B sections the audio stream into content blocks and filler blocks, responsive to analyzing an audio stream. In some embodiments of the invention, the playback pacing program 110A, 110B may analyze the audio stream by using natural language processing techniques to identify and extract natural language and transcribe the natural language into a text format for further analysis and annotation. Analyzing the audio stream may include speech segmentation to split the speech into words, part of speech tagging to identify the part of speech of each word, syntactic analysis to identify, among other things, sentence breaks and punctuation marks, et cetera. The playback pacing program 110A, 110B may utilize the transcription to section the audio stream into content blocks and filler blocks, by further analyzing the text comprising the transcript of the audio stream to determine what portions of the text comprise content blocks and what portions of the text comprise filler blocks and add annotations to the transcript delineating the respective sections. The playback pacing program 110A, 110B may detect and tag filler content using supervised learning techniques against known recurring filler content such as musical segues, introduction material such as phrases including "subscribe to my channel" or "hi welcome to the show," advertising phrases such as "this show brought to you by . . . " or "and now a word from our sponsor," et cetera. The playback pacing program 110A, 110B may tag any speech that is not considered filler blocks as content blocks; in some embodiments of the invention, the playback pacing program 110A, 110B utilizes supervised learning techniques against known recurring characteristics of content blocks, such as phrases including "what we're seeing here is" or "what you have to understand is." In some embodiments of the invention, the playback pacing program 110A, 110B may section the audio stream based on analyzing the prosody of the natural language in the audio stream and/or based on a template. The audio stream may comprise metadata indicating, among other things, the series and/or format associated with the audio stream; the playback pacing program 110A, 110B may select a template from a template repository based on matching the metadata associated with the audio stream with the metadata associated with the template, such that the audio stream conforms as accurately as possible to the selected template.

At 204, the playback pacing program 110A, 110B determines the subject matter and complexity of the content blocks. The playback pacing program 110A, 110B may determine the subject matter of the content blocks by analyzing the discourse semantics of the audio stream to perform topic segmentation and recognition. Topic segmentation and recognition may be achieved using any number of methods, including, for example, Hidden Markov Models, lexical chains, passage similarity using word co-occurrence, clustering, topic modeling, et cetera. In some embodiments of the invention, the playback pacing program 110A, 110B may initially section the audio stream into filler blocks and non-filler blocks and use topic segmentation and recognition to identify the topics of the non-filler blocks and accordingly divide the non-filler blocks into content blocks based on the topics. The playback pacing program 110A, 110B may annotate the transcript and/or the audio stream to record each topic and the content block with which the topic is associated.

The playback pacing program 110A, 110B may determine the complexity of the content blocks by measuring the linguistic complexity of the content blocks as a function of lexical readability and/or lexical richness. Lexical readability may be a metric of complexity based on how hard a text is to read, and may be, for example, a function of the average sentence length and average word syllables of the content block. Lexical richness may be a metric of complexity based on the variety of unique words, and may be, for example, a function of the total number of unique words in the content block or the number of words that only occur once divided by the total number of words. In some embodiments of the invention, the playback pacing program 110A, 110B may determine the complexity of the content blocks based on the topic; for example, general and/or simple topics, such as "pop culture news" or "cute animal reactions," may require very little background knowledge, familiarity, or concentration to digest. On the other hand, more specific and detailed topics, such as "discussion of three-photon interference" or "effects of Alice on patent examination 2013-present" may require specialized knowledge in or familiarity with dense technical fields, and/or may require above-average concentration to comprehend. Based on the complexity analysis, the playback pacing program 110A, 110B may assign a complexity score to each of the content blocks.

At 206, the playback pacing program 110A, 110B determines a level of interest and level of comprehension of the subject matter topics for a listener based on listener data. The level of interest may be based on any number of combination of indications of interest entered by the listener, listening history associated with the listener, personal interests of the listener, and learning goals entered by the listener. The indication of interest entered by the listener may be an explicit indication of topics and/or formats and/or series of audio streams that the listener is interested in listening to, entered into the playback pacing program 110A, 110B for example in response to a prompt or survey. The historical data may include audio streams that the listener has listened to in the past. The personal interests of the listener may be topics that the listener may be interested in listening to audio streams about, extrapolated for example based on a similarity to the listener's expressed interests, listening history, et cetera. The learning goals may be topics which the listener has expressed a desire to learn more about or to acquire a deep understanding of, for example in response to a prompt sent by the playback pacing program 110A, 110B; while a listener may be interested in some topics, the listener may desire a deeper understanding of topics that the listener is not necessarily interested in, for example tax preparation or business operations, and which therefore may not be necessarily reflected in the listener's personal preferences. In some embodiments of the invention, the learning goals may further comprise an amount of total time the listener has available to listen to the audio stream, and/or an amount of time the listener wants to spend on certain topics. In some embodiments of the invention, the learning goals may comprise a preferred level of comprehension, which represents the level of comprehension that the listener wants to achieve for a given topic. For example, whether the listener just wants an overview of a topic or whether the listener wants to comprehend the topic on a deeper level. The playback pacing program 110A, 110B may, for any given topic, generate an interest score associated with the listener based on the determined level of interest.

In some embodiments of the invention, the playback pacing program 110A, 110B may determine a level of comprehension of the listener with respect to the topics. The level of comprehension may be based on, for example, the listener's self-assessment, listening history of the listener, and learning assessments such as competency-based learning. The listener may be prompted to assess their own comprehension of a given topic. The playback pacing program 110A, 110B may also infer level of comprehension from the listening history of the listener; if the listener has listened to many content blocks in the past that were on topics similar to the topics in the current audio stream, the playback pacing program 110A, 110B may infer that the listener has a high level of comprehension for the topic. The level of comprehension may be based on how quickly the listener picked up concepts or new topics in the past. In some embodiments of the invention, for example where the listener's comprehension of the topic was assessed while listening to the audio stream using biometric sensors, the level of comprehension may be based on past comprehension assessments of similar topics. The playback pacing program 110A, 110B may assign a comprehension score to a given topic based on the level of comprehension associated with the listener.

At 208, based on the level of interest, level of comprehension, context of a subject matter topic, and learning objectives of the listener, the playback pacing program 110A, 110B assigns an audio speed to the content blocks based on the associated subject matter topic. For content blocks associated with dense topics, or topics where the complexity score associated with the content block exceeds an upper complexity threshold, the playback pacing program 110A, 110B may normalize the assigned playback speed of the content block to a lower default speed value, which may be, for example, 140 words per minute. For content blocks associated with topics that are easy to comprehend, or topics where the complexity score of the content block falls below a lower complexity threshold, the playback pacing program 110A, 110B may normalize the assigned playback speed of the content block to an upper default speed value, for example 160 words per minute. The playback pacing program 110A, 110B may then adjust the assigned playback speed of these starting speed values upwards or downwards based on the comprehension score and interest score associated with the listener, and the complexity score associated with the content block. For example, as the complexity score associated with the content block falls, the comprehension scores and/or interest scores associated with the listener rise, the higher the playback speed that the playback pacing program 110A, 110B assigns to the content block. Conversely, as the complexity score associated with the content block rises, the comprehension scores and/or interest scores associated with the listener fall, the lower the playback speed that the playback pacing program 110A, 110B assigns to the content block. For example, sports news highlights are simple and easy to comprehend and can be listened to at high speeds, while physics lectures are dense and difficult to comprehend and must be listened to at a lower speed. Once the playback pacing program 110A, 110B has applied the effects of the complexity, comprehension, and interest scores to the default speed values, the playback pacing program 110A, 110B may assign the playback speed to the content block.

At 210, the playback pacing program 110A, 110B normalizes the content blocks to the assigned audio speed. The playback pacing program 110A, 110B may apply the assigned playback speed to the content block by ingesting the audio stream and depending on the native playback speed of the content block relative to the assigned playback speed, speed up or slow down playback of the audio stream, for example by synthesizing speech based on the transcript at the desired playback speed. The playback pacing program 110A, 110B may additionally or alternatively modify the audio stream by partially or entirely removing filler blocks, and/or by partially or entirely removing content blocks, for example removing those content blocks pertaining to topics for which the listener's interest score and/or comprehension score falls below a minimum threshold or removing sections of the content block that are not crucial for comprehending a prioritized topic.

At 212, based on real-time biometric information of the listener, the playback pacing program 110A, 110B dynamically modifies the audio speed of the content blocks during playback of the audio stream to the listener. The playback pacing program 110A, 110B may, based on real-time biometric information of the listener, dynamically modify the playback speed of the content blocks during playback of the audio stream to the listener. The playback pacing program 110A, 110B may, using sensors 108 such as cameras or EEG machines, and subject to listener's approval, collect real-time biometric data to determine a listener's level of comprehension based on a detected sentiment of the listener in real time as the listener is listening to the audio stream. The listener's sentiment may include confusion or frustration, which may be, for example, inferred from sensor data indicating dilated pupils, an elevated heart rate, furrowing of the brow, frowning, exasperated noises, et cetera. The listener's sentiment may further include boredom, which may, for example, be inferred from sensor data indicating above-average eye movement, yawning, fidgeting, sighing, et cetera. If the playback pacing program 110A, 110B determines, based on the sensor data, that the listener is expressing confusion or frustration, the playback pacing program 110A, 110B may decrease the playback speed of the current content block to allow the listener more time to process the content block, improving comprehension and reducing frustration. If the playback pacing program 110A, 110B determines based on the sensor data that the listener is expressing distraction or boredom, the playback pacing program 110A, 110B may increase playback speed of the current content block to increase the listener's stimulation and increase interest or may skip the current content block and/or move to a content block associated with a topic that has a higher interest score. In some embodiments of the invention, the playback pacing program 110A, 110B may adjust the complexity scores, interest scores, and/or comprehension scores of a listener with respect to the topic of the currently consumed content block.

Figure 3:
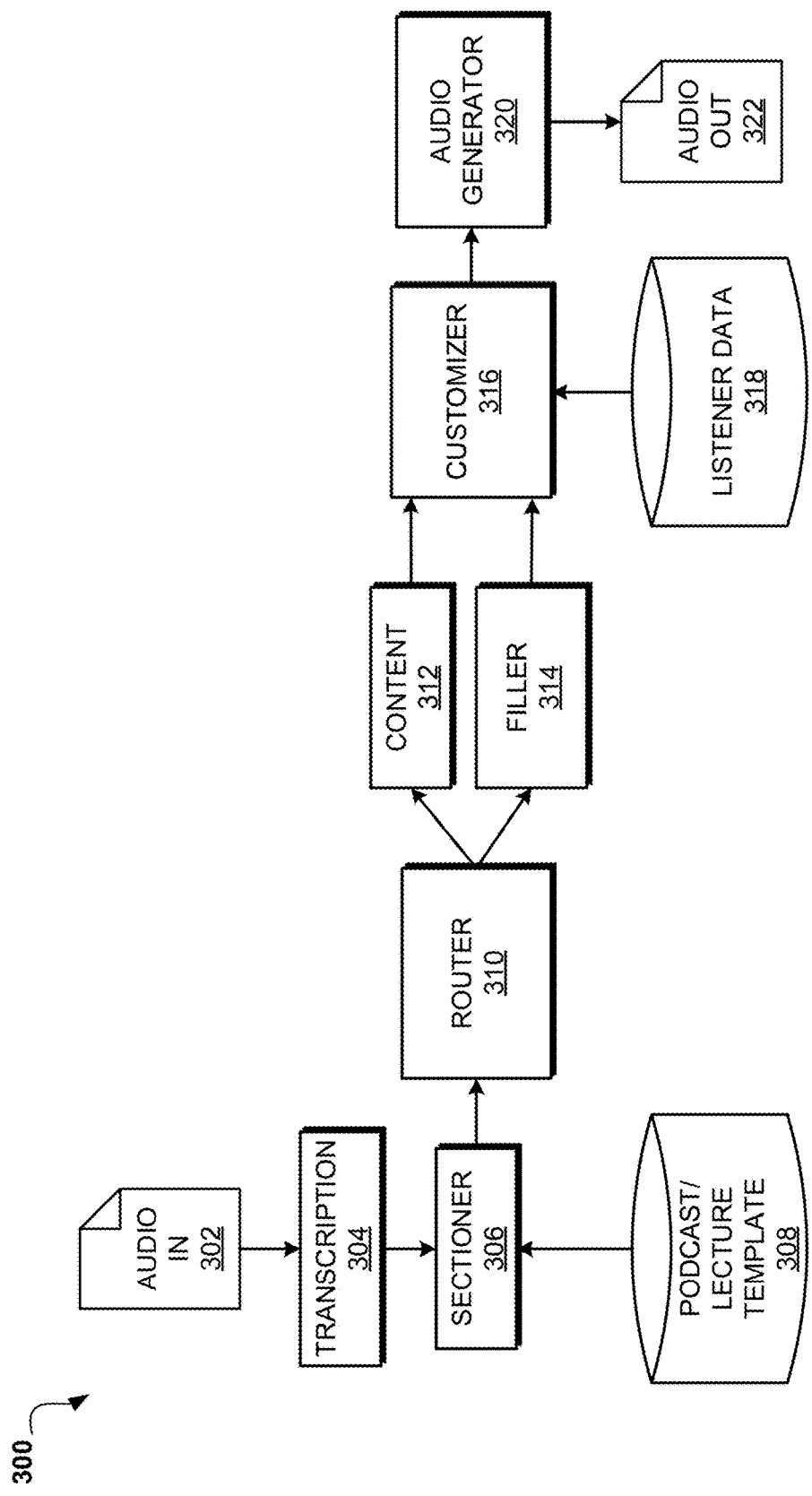
FIG. 3 is a block diagram illustrating an exemplary system implementing the playback pacing process according to at least one embodiment.

Referring now to FIG. 3, a block diagram illustrating an exemplary system 300 implementing the playback pacing process 200 is depicted according to at least one embodiment. Here, an audio stream 302 is fed as an input into the transcription module 304. The transcription module 304 transcribes the audio into a textual format, or transcript, using natural language processing techniques. The transcription module 304 then provides the transcript of the input audio to the sectioner module 306. In some embodiments, the transcription module 304 may further extract, and provide to the sectioner module 306, prosodic information from the audio stream 302. The sectioner module 306 may also receive a podcast/lecture template 308, which may be selected from a repository of templates by playback pacing program 110A, 110B. Based on the podcast/lecture template 308 and the transcript, sectioner module 306 divides the audio stream 302 into blocks and provides the blocks to router 310. Router module 310 splits the provided blocks into content blocks 312 and filler blocks 314, which are passed to the customizer module 316. The customizer module 316 receives listener data 318, which may comprise data pertaining to a listener's interest or comprehension of the topics associated with the content blocks 312 including, for example, indications of interest entered by the listener, listening history associated with the listener, personal interests of the listener, and learning goals entered by the listener. The customizer module 316 may utilize the listener data 318 to calculate a comprehension score and an interest score for the topics associated with the content blocks 312. Based on the listener data 318 and/or the comprehension score, interest score, and complexity score, the customizer module 316 may assign a playback speed to the content 312. The customizer module 316 may pass the assigned playback speed and metadata indicating the corresponding content block 312 to audio generator 320, which modifies the content block 312 to play at the assigned playback speed, and outputs the modified content block 322 for playback to the listener.

Figure 4:
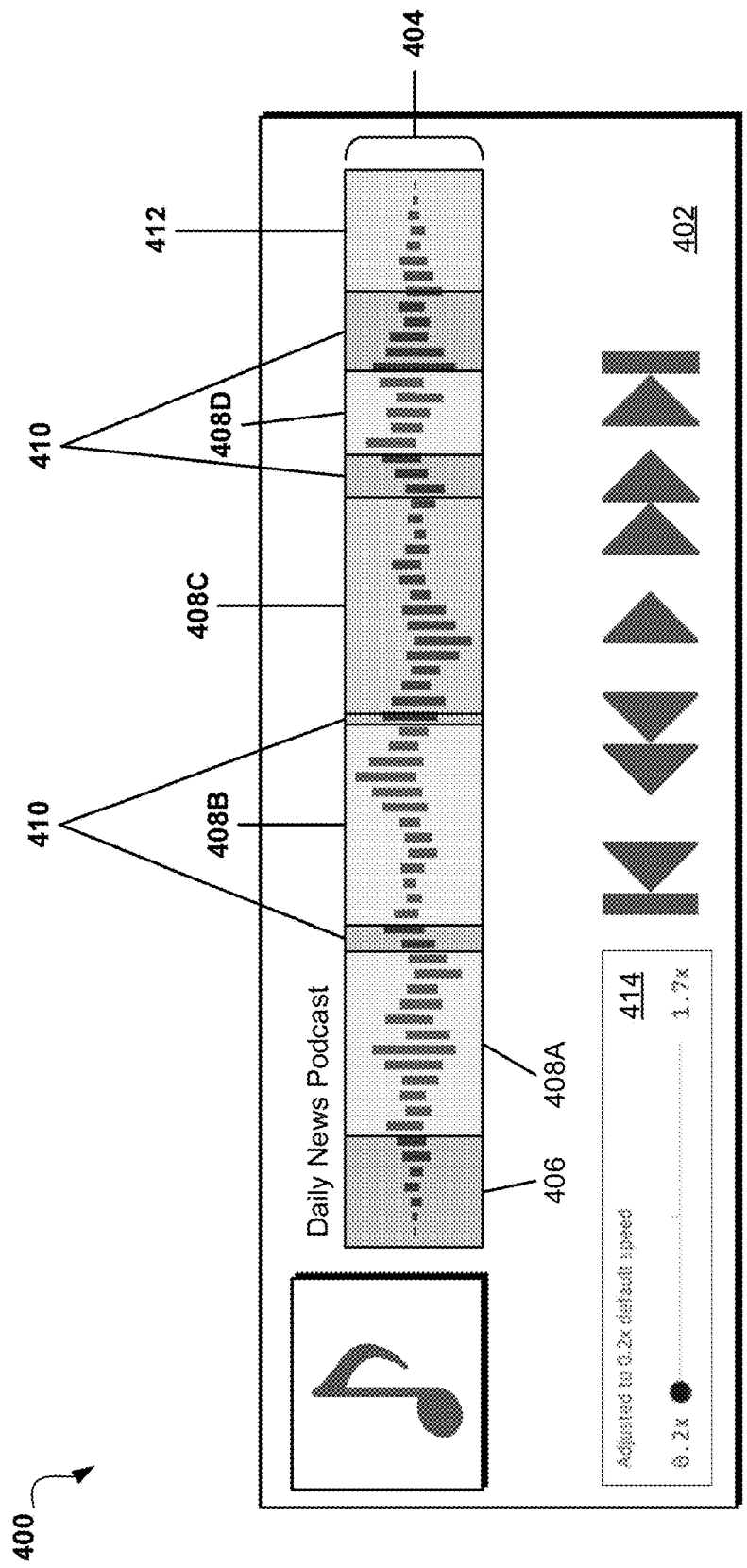
FIG. 4 illustrates an exemplary graphical interface element of the playback pacing process according to at least one embodiment.

Referring now to FIG. 4, an exemplary graphical interface element 400 of the playback pacing process 200 is depicted according to at least one embodiment. Here, a media player 402 comprises at least a visualizer 404, which graphically represents the audio stream 302. The playback pacing program 110A, 110B has sectioned the audio stream 302 into a series of blocks, comprising an introduction 406, discussion segments 408, where discussion segment 408A is associated with a first topic, discussion segment 408B is associated with a second topic, discussion segment 408C is associated with a third topic, and discussion segment 408D is associated with a fourth topic. The blocks further comprise transitional segments 410 disposed between the discussion segments 408 and serving to segue the discussion from one topic to another, and outro segment 412, which comprises farewells, outro music, and show notes. The introduction 406, transitional segments 410, and outro segment 412 may be identified and flagged as filler blocks 314, and the discussion segments 408 may be identified and flagged as content blocks 312. The blocks may be represented as monochromatic rectangles, overlaid on visualizer 404 and translucent enough to make visualizer 404 visible while clearly delineating the time series of the podcast comprising the block. The monochromatic rectangles representing the blocks may be color-coded to indicate whether the block is a filler block 314 or content block 312. In some embodiments of the invention, media player 402 may further comprise playback speed controls 414, which may allow a listener to adjust the speed of the audio stream 302 or select a block and adjust the playback speed of only the selected block. The selected block may be a filler block 314 or content block 312. The playback speed controls 414 may be configured to allow the listener to adjust a sliding scale within a range comprising a lower bound, here 0.2× speed, and an upper bound, here 1.7× speed. The range may be based on the playback speed assigned to the selected block, for example such that the median value of the range is the assigned playback speed.

It may be appreciated that FIGS. 2-4 provides only an illustration of one implementation and does not imply any limitations with regard to how different embodiments may be implemented. Many modifications to the depicted environments may be made based on design and implementation requirements.

Figure 5:
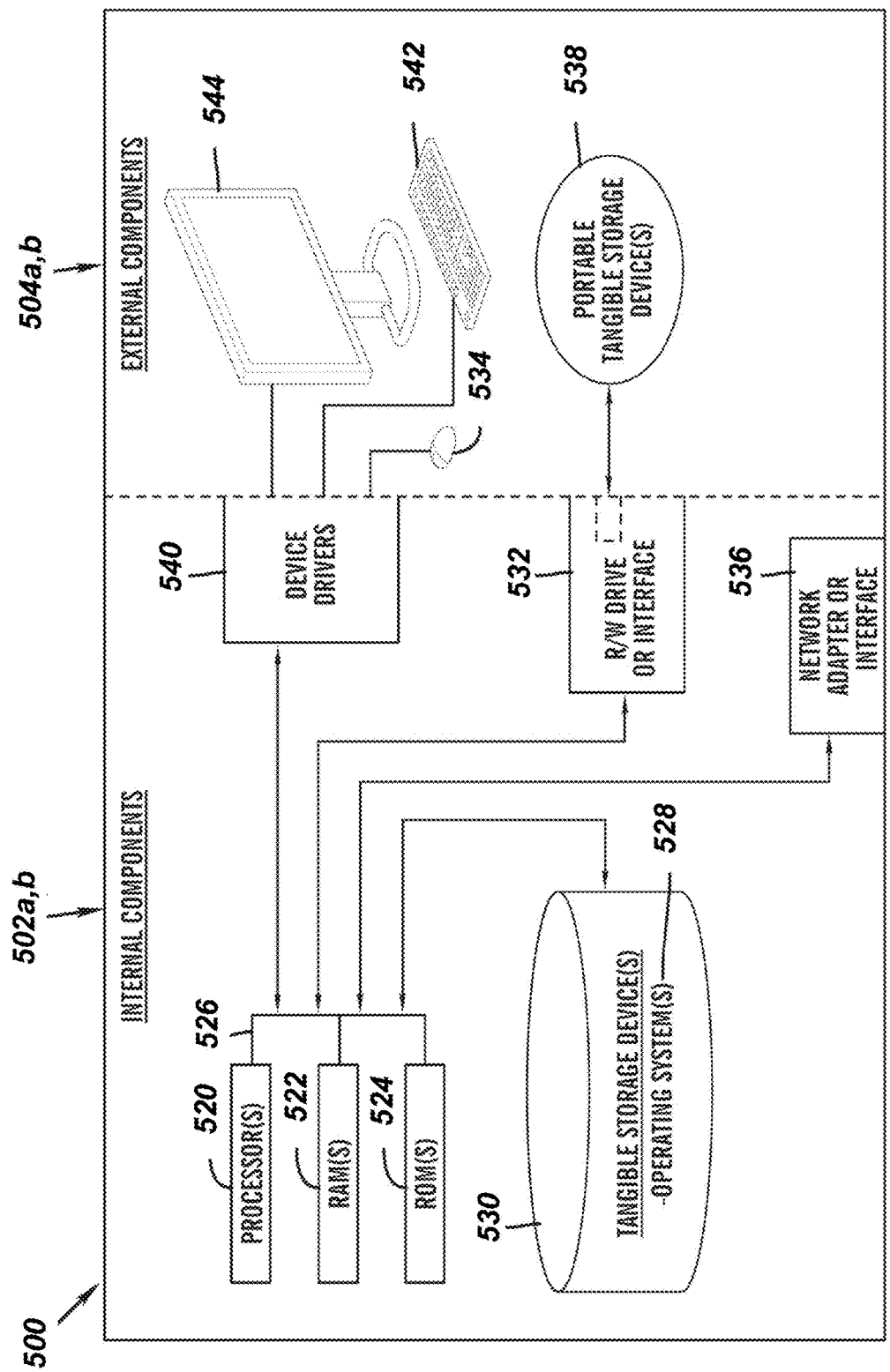
FIG. 5 is a block diagram of internal and external components of computers and servers depicted in FIG. 1 according to at least one embodiment.

FIG. 5 is a block diagram 500 of internal and external components of the client computing device 102 and the server 112 depicted in FIG. 1 in accordance with an embodiment of the present invention. It should be appreciated that FIG. 5 provides only an illustration of one implementation and does not imply any limitations with regard to the environments in which different embodiments may be implemented. Many modifications to the depicted environments may be made based on design and implementation requirements.

The data processing system 502, 504 is representative of any electronic device capable of executing machine-readable program instructions. The data processing system 502, 504 may be representative of a smart phone, a computer system, PDA, or other electronic devices. Examples of computing systems, environments, and/or configurations that may represented by the data processing system 502, 504 include, but are not limited to, personal computer systems, server computer systems, thin clients, thick clients, handheld or laptop devices, multiprocessor systems, microprocessor-based systems, network PCs, minicomputer systems, and distributed cloud computing environments that include any of the above systems or devices.

The client computing device 102 and the server 112 may include respective sets of internal components 502a,b and external components 504a,b illustrated in FIG. 5. Each of the sets of internal components 502 include one or more processors 520, one or more computer-readable RAMs 522, and one or more computer-readable ROMs 524 on one or more buses 526, and one or more operating systems 528 and one or more computer-readable tangible storage devices 530. The one or more operating systems 528, the playback pacing program 110A in the client computing device 102, and the playback pacing program 110B in the server 112 are stored on one or more of the respective computer-readable tangible storage devices 530 for execution by one or more of the respective processors 520 via one or more of the respective RAMs 522 (which typically include cache memory). In the embodiment illustrated in FIG. 5, each of the computer-readable tangible storage devices 530 is a magnetic disk storage device of an internal hard drive. Alternatively, each of the computer-readable tangible storage devices 530 is a semiconductor storage device such as ROM 524, EPROM, flash memory or any other computer-readable tangible storage device that can store a computer program and digital information.

Each set of internal components 502a,b also includes a RAY drive or interface 532 to read from and write to one or more portable computer-readable tangible storage devices 538 such as a CD-ROM, DVD, memory stick, magnetic tape, magnetic disk, optical disk or semiconductor storage device. A software program, such as the playback pacing program 110A, 110B, can be stored on one or more of the respective portable computer-readable tangible storage devices 538, read via the respective RAY drive or interface 532, and loaded into the respective hard drive 530.

Each set of internal components 502a,b also includes network adapters or interfaces 536 such as a TCP/IP adapter cards, wireless Wi-Fi interface cards, or 3G or 4G wireless interface cards or other wired or wireless communication links. The playback pacing program 110A in the client computing device 102 and the playback pacing program 110B in the server 112 can be downloaded to the client computing device 102 and the server 112 from an external computer via a network (for example, the Internet, a local area network or other, wide area network) and respective network adapters or interfaces 536. From the network adapters or interfaces 536, the playback pacing program 110A in the client computing device 102 and the playback pacing program 110B in the server 112 are loaded into the respective hard drive 530. The network may comprise copper wires, optical fibers, wireless transmission, routers, firewalls, switches, gateway computers and/or edge servers.

Each of the sets of external components 504a,b can include a computer display monitor 544, a keyboard 542, and a computer mouse 534. External components 504a,b can also include touch screens, virtual keyboards, touch pads, pointing devices, and other human interface devices. Each of the sets of internal components 502a,b also includes device drivers 540 to interface to computer display monitor 544, keyboard 542, and computer mouse 534. The device drivers 540, RAY drive or interface 532, and network adapter or interface 536 comprise hardware and software (stored in storage device 530 and/or ROM 524).

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as Follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as Follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as Follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 6:
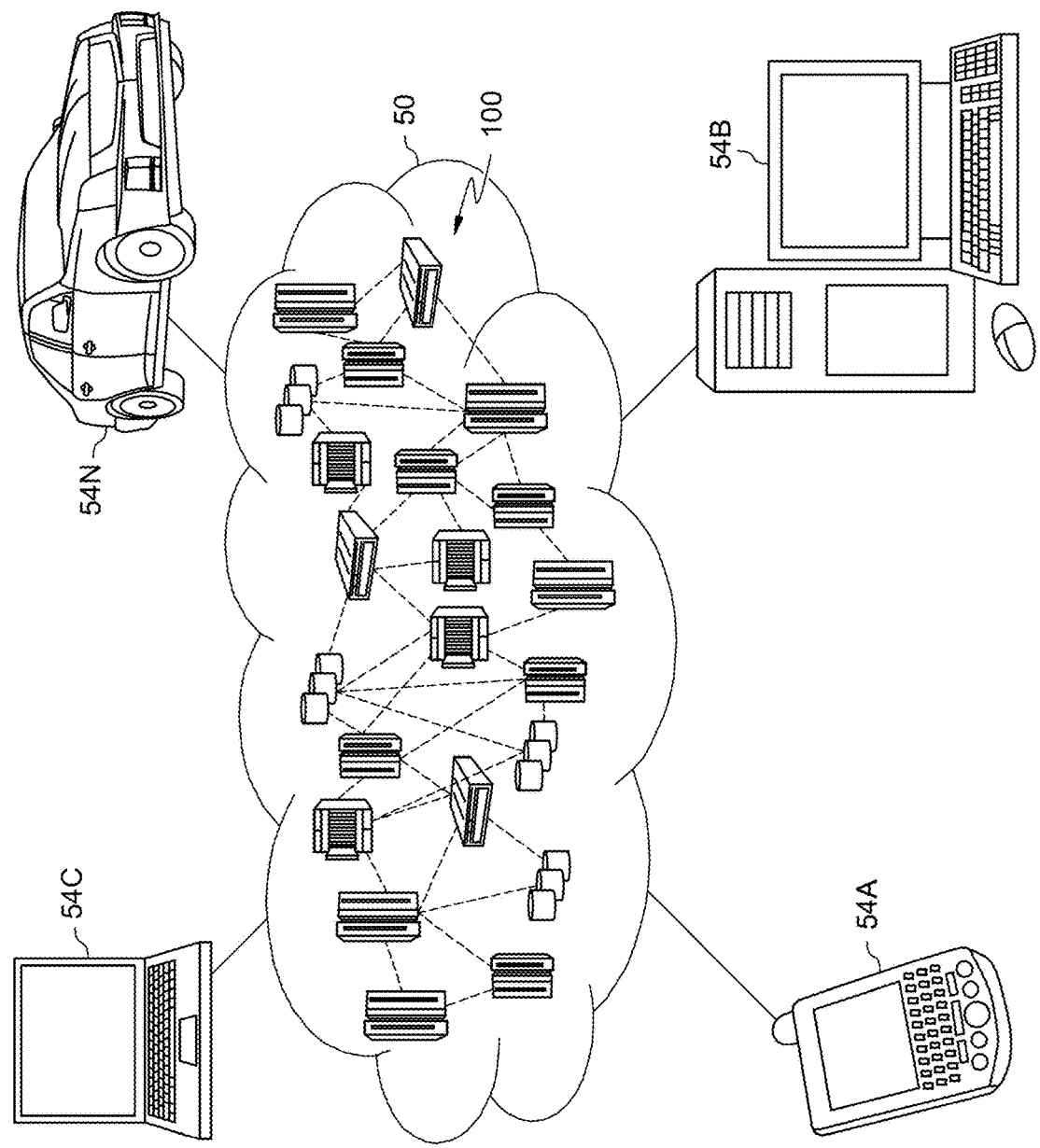
FIG. 6 depicts a cloud computing environment according to an embodiment of the present invention.

Referring now to FIG. 6, illustrative cloud computing environment 50 is depicted. As shown, cloud computing environment 50 comprises one or more cloud computing nodes 100 with which local computing devices used by cloud consumers, such as, for example, personal digital assistant (PDA) or cellular telephone 54A, desktop computer 54B, laptop computer 54C, and/or automobile computer system 54N may communicate. Nodes 100 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 6 are intended to be illustrative only and that computing nodes 100 and cloud computing environment 50 can communicate with any type of computerized device over any type of network and/or network addressable connection (e.g., using a web browser).

Figure 7:
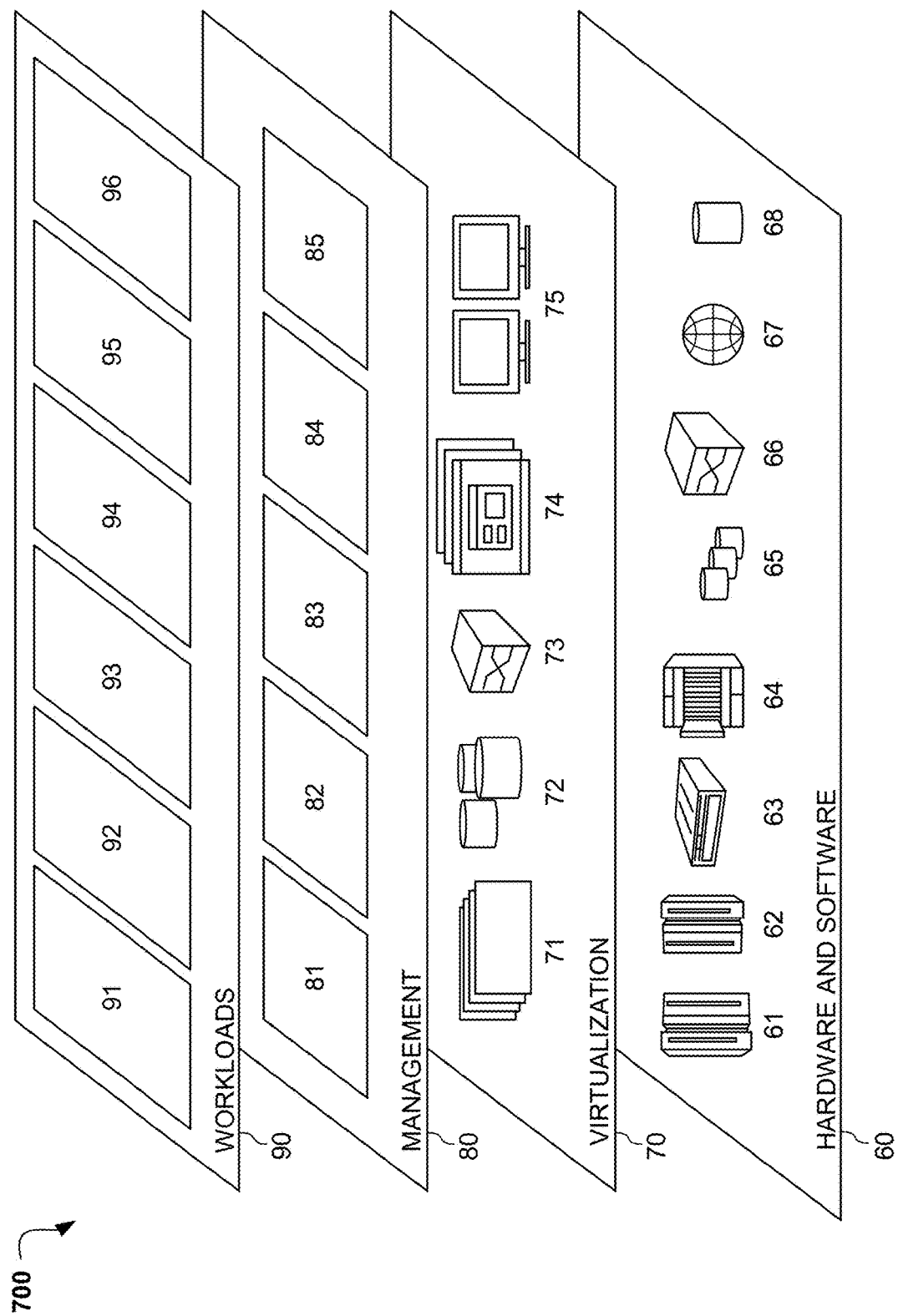
FIG. 7 depicts abstraction model layers according to an embodiment of the present invention.

Referring now to FIG. 7, a set of functional abstraction layers 700 provided by cloud computing environment 50 is shown. It should be understood in advance that the components, layers, and functions shown in FIG. 7 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and playback pacing 96. The playback pacing 96 may be enabled to create a personalized media playback pacing based on the media content and listener data at the time of media consumption.

The descriptions of the various embodiments of the present invention have been presented for purposes of illustration but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A processor-implemented method for personalizing playback of an audio stream, the method comprising:
sectioning the audio stream into one or more content blocks and one or more filler blocks in real time as the audio stream is received through a network connection;
determining one or more topics associated with the one or more filler blocks;
determining a level of complexity associated with the one or more filler blocks;
determining a listener's level of interest in and level of comprehension of the one or more topics;
based on the level of complexity, the level of interest, and level of comprehension corresponding to the one or more topics, assigning a playback speed to the one or more content blocks associated with the one or more topics; and playing the one or more content blocks to the listener at the assigned playback speed.

2. The method of claim 1, wherein the level of interest is based on one or more learning goals provided by the listener.

3. The method of claim 1, further comprising:
modifying the audio stream to remove one or more content blocks based on a level of interest corresponding to one or more topics associated with the one or more content blocks falling below a minimum threshold.

4. The method of claim 1, further comprising:
responsive to identifying a sentiment of the listener based on recording sensor data from one or more sensors, dynamically modifying the playback speed of a currently played content block of the one or more content blocks based on the identified sentiment of the listener.

5. The method of claim 1, wherein the assigned playback speed of a content block of the one or more content blocks is modified from an upper default speed value responsive to the level of complexity of a topic associated with the content block of the one or more content blocks falling below a lower complexity threshold.

6. The method of claim 1, wherein the assigned playback speed of a content block of the one or more content blocks is modified from a lower default speed value responsive to the level of complexity of a topic associated with the content block of the one or more content blocks exceeding an upper complexity threshold.

7. The method of claim 1, wherein at least one topic of the one or more topics comprises one or more subtopics, and one or more of the one or more content blocks are associated with the one or more subtopics.

8. A computer system for personalizing playback of an audio stream, the computer system comprising:
one or more processors, one or more computer-readable memories, one or more computer-readable tangible storage medium, and program instructions stored on at least one of the one or more tangible storage medium for execution by at least one of the one or more processors via at least one of the one or more memories, wherein the computer system is capable of performing a method comprising:
sectioning the audio stream into one or more content blocks and one or more filler blocks in real time as the audio stream is received through a network connection;
determining one or more topics associated with the one or more filler blocks;
determining a level of complexity associated with the one or more filler blocks;
determining a listener's level of interest in and level of comprehension of the one or more topics;
based on the level of complexity, the level of interest, and level of comprehension corresponding to the one or more topics, assigning a playback speed to the one or more content blocks associated with the one or more topics; and
playing the one or more content blocks to the listener at the assigned playback speed.

9. The computer system of claim 8, wherein the level of interest is based on one or more learning goals provided by the listener.

10. The computer system of claim 8, further comprising:
modifying the audio stream to remove one or more content blocks based on a level of interest corresponding to one or more topics associated with the one or more content blocks falling below a minimum threshold.

11. The computer system of claim 8, further comprising:
responsive to identifying a sentiment of the listener based on recording sensor data from one or more sensors, dynamically modifying the playback speed of a currently played content block of the one or more content blocks based on the identified sentiment of the listener.

12. The computer system of claim 8, wherein the assigned playback speed of a content block of the one or more content blocks is modified from an upper default speed value responsive to the level of complexity of a topic associated with the content block of the one or more content blocks falling below a lower complexity threshold.

13. The computer system of claim 8, wherein the assigned playback speed of a content block of the one or more content blocks is modified from a lower default speed value responsive to the level of complexity of a topic associated with the content block of the one or more content blocks exceeding an upper complexity threshold.

14. The computer system of claim 8, wherein at least one topic of the one or more topics comprises one or more subtopics, and one or more of the one or more content blocks are associated with the one or more subtopics.

15. A computer program product for personalizing playback of an audio stream, the computer program product comprising:
one or more computer-readable tangible storage medium and program instructions stored on at least one of the one or more tangible storage medium, the program instructions executable by a processor to cause the processor to perform a method comprising:
sectioning the audio stream into one or more content blocks and one or more filler blocks in real time as the audio stream is received through a network connection;
determining one or more topics associated with the one or more filler blocks;
determining a level of complexity associated with the one or more filler blocks;
determining a listener's level of interest in and level of comprehension of the one or more topics;
based on the level of complexity, the level of interest, and level of comprehension corresponding to the one or more topics, assigning a playback speed to the one or more content blocks associated with the one or more topics; and
playing the one or more content blocks to the listener at the assigned playback speed.

16. The computer program product of claim 15, wherein the level of interest is based on one or more learning goals provided by the listener.

17. The computer program product of claim 15, further comprising:
modifying the audio stream to remove one or more content blocks based on a level of interest corresponding to one or more topics associated with the one or more content blocks falling below a minimum threshold.

18. The computer program product of claim 15, responsive to identifying a sentiment of the listener based on recording sensor data from one or more sensors, dynamically modifying the playback speed of a currently played content block of the one or more content blocks based on the identified sentiment of the listener.

19. The computer program product of claim 15, wherein the assigned playback speed of a content block of the one or more content blocks is modified from an upper default speed value responsive to the level of complexity of a topic associated with the content block of the one or more content blocks falling below a lower complexity threshold.

20. The computer program product of claim 15, wherein the assigned playback speed of a content block of the one or more content blocks is modified from a lower default speed value responsive to the level of complexity of a topic associated with the content block of the one or more content blocks exceeding an upper complexity threshold.

* * * * *